United States Patent [19]
Hauptmann et al.

[11] Patent Number: 5,688,263
[45] Date of Patent: Nov. 18, 1997

[54] LASER SURGERY APPLICATOR

[75] Inventors: Gerhard Hauptmann, München; Werner Rother, Weiterstadt, both of Germany

[73] Assignee: Dornier Medizintechnik GmbH, Germany

[21] Appl. No.: 577,102

[22] Filed: Dec. 22, 1995

[30] Foreign Application Priority Data

Dec. 22, 1994 [DE] Germany ................. 44 45 908.4

[51] Int. Cl.⁶ ................................................. A61B 17/36
[52] U.S. Cl. ........................................ 606/13; 606/17
[58] Field of Search .................... 606/14, 15, 16, 606/17, 4, 5, 6, 10, 11, 12

[56] References Cited

U.S. PATENT DOCUMENTS

| | | | |
|---|---|---|---|
| 4,660,925 | 4/1987 | McCaughan, Jr. | 606/16 X |
| 4,693,244 | 9/1987 | Daikuzono. | |
| 4,718,417 | 1/1988 | Kittrell et al. | 606/15 |
| 5,354,294 | 10/1994 | Chou. | |
| 5,415,655 | 5/1995 | Fuller et al. | 606/16 |
| 5,454,782 | 10/1995 | Perkins | 606/15 X |
| 5,495,541 | 2/1996 | Murray et al. | 606/17 X |
| 5,496,307 | 3/1996 | Daikuzono | 606/15 |
| 5,562,657 | 10/1996 | Griffin | 606/15 |
| 5,562,658 | 10/1996 | Long | 606/15 |

FOREIGN PATENT DOCUMENTS

| | | |
|---|---|---|
| 0 514 258 | 11/1992 | European Pat. Off. . |
| 31 19 322 | 1/1986 | Germany . |
| 39 18 965 | 3/1992 | Germany . |
| 92/17243 | 10/1992 | WIPO . |

*Primary Examiner*—Jennifer Bahr
*Assistant Examiner*—Sonya Harris-Ogugua
*Attorney, Agent, or Firm*—Evenson, McKeown, Edwards & Lenahan P.L.L.C.

[57] ABSTRACT

The laser surgical applicator according to the invention is used for contact vaporization of tissue and has a light guide with a quartz glass core at whose distal end a contact tip made of an optically transparent solid material is located. The contact tip has a quartz glass sheath in which at least the quartz glass core of the light guide runs coaxially at a distance from the inside wall and the distal end of the quartz glass core is molten with the distal end of the quartz glass sheath to form an optically transparent tip.

8 Claims, 2 Drawing Sheets

LASER SURGERY APPLICATOR

BACKGROUND AND SUMMARY OF THE INVENTION

The invention relates to a laser surgical apparatus for contact vaporization of tissue, in which a light guide fiber with a quartz glass core has a contact tip made of a quartz glass sheath at its distal end. The distal end of the quartz glass core is melted together with the distal end of the quartz glass sheath to form an optically transparent tip. (The terms "distal" and "proximal" here and in the following text relate to proximity to the radiation source, in other words the laser device.)

For vaporization of tissue using Nd:YAG laser radiation, high power densities are required at the tissue, and hence a high laser power is necessary. Many types of tissue initially have a reflecting liquid film on their surfaces, which deflects the laser radiation and can cause secondary injuries. For this reason, there has long been a recognized need for so-called contact vaporization, which was first made possible by means of a sapphire tip (e.g. U.S. Pat. No. 4,593,244) mounted on the end of the light guide which conducts the laser radiation. However, such applicators are very complex in design because it is necessary to cool the junction between the sapphire and the light guide; also, the sapphire is relatively expensive, and there is the danger that if the cooling should fail, the junction between the sapphire and light guide would be overheated, causing the sapphire tip to fall off.

European patent document EP 0 514 258 A1 discloses an applicator of the type recited above in which a cylindrical sheath surrounds the end of a light guide and is fused with the latter to form a contact tip. The close fit between the sheath and the light guide means that the melting area cannot be set exactly, so that the area from which the laser light leaves the contact tip likewise cannot be determined in advance. In addition the laser light diverges substantially as it exits the contact tip, especially when diode lasers are used.

An optically transparent hollow needle made of plastic is disclosed in international patent document WO 92/17243. The free end of a light guide terminates in the needle, which can be inserted into the tissue. However, this applicator is intended for hyperthermia and cannot be used for vaporization because of the material used (plastic). A translucent cap that is slid over the sheathed end of a light guide is also described in German patent document DE 39 19 322 C2. However, this probe is also usable only for hyperthermia; also, the laser light within the cap emerges from the light guide and must pass through the walls of the cap first, as in the case of the above-mentioned international patent document WO 92/17243.

The purpose of the present invention is to provide a laser surgery applicator for contact vaporization of tissue which is simple and inexpensive, meets the higher safety requirements of laser surgery, and permits improved convergence of the emitted laser light, especially when diode lasers are used.

In contrast to tips mounted according to the prior art, in the present invention there is no longer an air gap that would attenuate the laser radiation between the light guide and the tip, which gap must be overcome by the light before it leaves the contact tip. A funnel-shaped transition between the light guide and the contact tip has the effect that these light beams that are travelling with a large aperture are bundled inside the tunnel-shaped transition and converge as they emerge from convex contact tips in particular. As a result, the laser radiation is focused, and a high power density is achieved at the transition between the applicator and the tissue. This power density facilitates a rapid heating of the tissue, and hence rapid development of a carbonization "seed." Immediately after this carbonization "seed" develops, further laser radiation is highly absorbed by the carbonization layer, so that the carbonization process can be maintained over a large area.

The melting process also produces a mechanically strong connection between the contact tip and the light guide, with centering of the latter being required only during the manufacturing process. If the jacket layer (buffer) of the light guide must also consist of quartz glass, it may be included in the melt with the quartz glass sheath.

To adjust to various anatomical conditions and changes in the radiation characteristic, the molten area can also be made wedge- and/or cone-shaped, with these areas always being made only large enough to be picked up by the divergent light from the light guide.

Other objects, advantages and novel features of the present invention will become apparent from the following detailed description of the invention when considered in conjunction with the accompanying drawings.

DETAILED DESCRIPTION OF THE DRAWINGS

Figure 1:
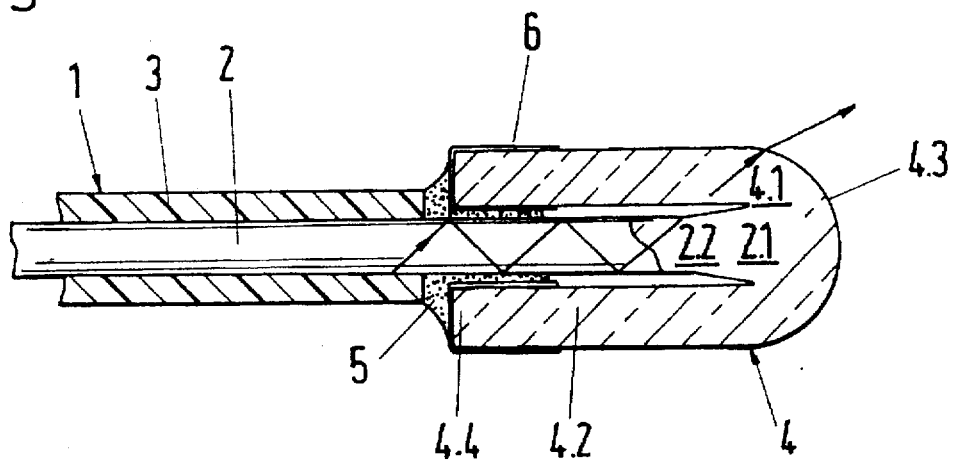
FIGS. 1 and 1a show a cross section through an applicator with a contact tip according to the invention.
Figure 1A:
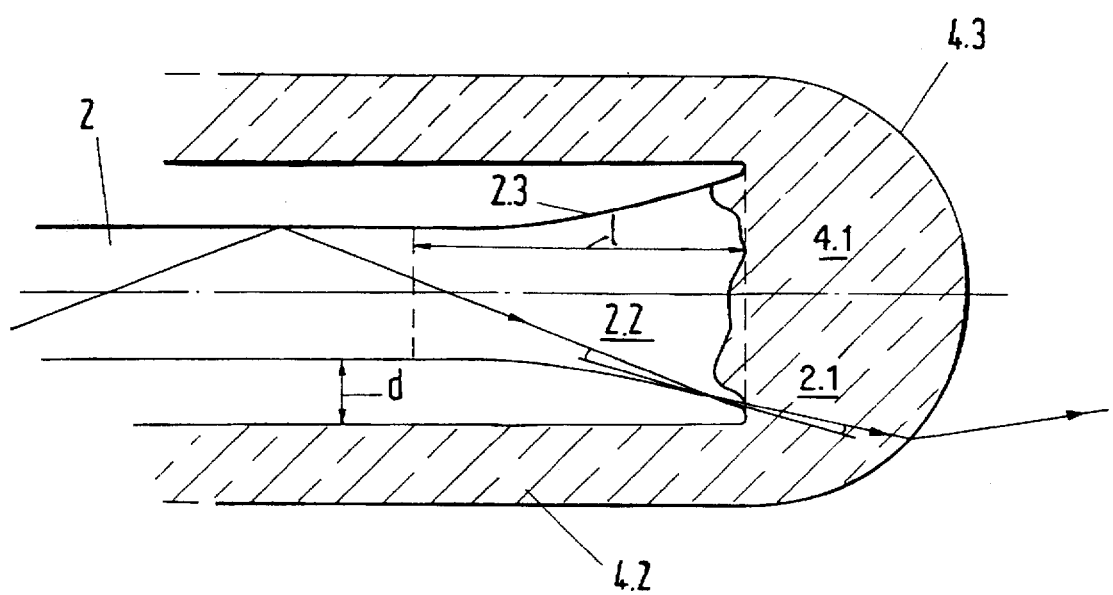

The applicator shown in FIGS. 1 and 1a has a light guide 1 with a quartz glass core 2 and plastic sheathing 3. The end of the sheathing 3 is removed from the last one to two cm of quartz glass core 2. Contact tip 4 consists of a quartz glass sheath 4.2, which surrounds core 2 of the light guide 1 in the shape of a mushroom, and is fused with the latter in areas 2.1 and 4.1 in such fashion that an optically transparent tip 4.3 with a hemispherical surface is formed, from which the laser radiation emerges. Between the inside wall of sheath 4.2 and the jacket surface of fiber core 2 there is a space d which is as constant as possible all the way around, bridged by the funnel-shaped transitional area 2.2. The optimum distance d is determined from the length l and the degree of expansion of the funnel. In a funnel with an aperture angle that increases from the inside to the outside, its optimum length l is determined by the point at which a light beam with a maximum aperture contacts the funnel jacket tangentially. In FIG. 1a a light beam is shown schematically near the aperture limit. Such a light beam, in the vicinity of funnel 2.2, strikes its curved jacket surface and from there is reflected in the direction of the optical axis of light guide 2. The convex outlet area of tip 4.3, further converges the emerging light.

To produce a contact tip according to FIG. 1a, a cylindrical quartz glass sheath is used, into which the jacketed end of a light guide core 2 is inserted. (If jacketing 3 of light guide 1 likewise consists of quartz glass, the jacket need not be peeled.) The end of the light guide that projects from the sheath is melted to form a drop-shaped thickening whose diameter corresponds at least to the inside diameter of the sheath, but is advantageously larger. A funnel-shaped transition 2.2 is then formed between the thickening and the remainder of the light guide. Distal ends 2.1 and 4.1 of light guide 1 and quartz glass sheath 4 are then heated to just below the softening point, whereupon they fuse to form a homogeneous glass body. Funnel-shaped transition 2.2 must be maintained in the final melting process. For a light guide diameter of 600 μm, which is typical in laser surgery, and a numerical aperture of 0.37 (corresponding to approximately 42° full angle) the optimum length 1 of the funnel is about 3 mm.

The distal end 4.4 of quartz glass sheath 4.2 is sealed off from light guide 1 by an adhesive collar 5, so that the contact tip can be used even when it is completely immersed in a liquid. The adhesive has a lower index of refraction than core 2 of light guide 1 so that in this area of core 2 total reflection is guaranteed for the laser radiation.

Since it is not completely avoidable that laser radiation will be reflected back into sheath 4 by surface 4.3, comparatively high temperatures can still develop at the proximal end of applicator 4.4. Therefore it can be advantageous to protect this area against radiation by means of a mirror coating 6; known metal or lambda/4 coatings are suitable for this purpose.

Figure 2:
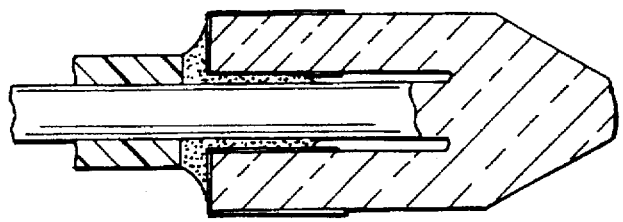
FIG. 2 is a cross section through an applicator with a chisel-shaped contact tip according to the invention.
Figure 3:
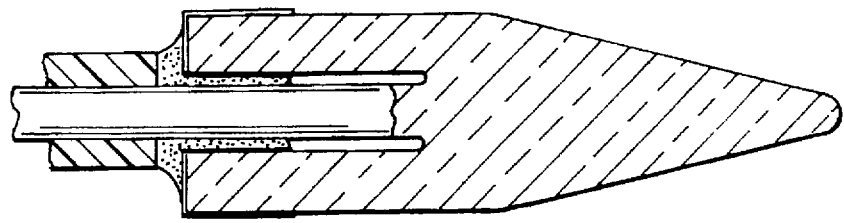
FIG. 3 is a cross section through an applicator with a conical contact tip according to the invention.
Figure 4:
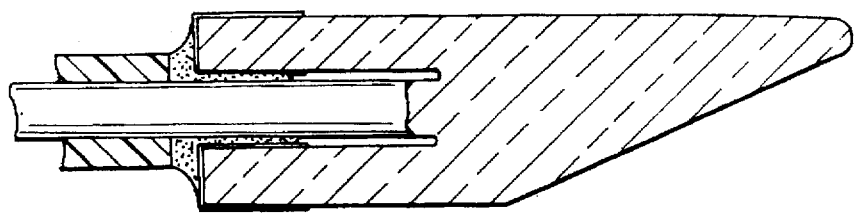
FIG. 4 is a cross section through an applicator with a contact tip flattened laterally according to the invention.

FIGS. 2, 3, and 4 show various embodiments of contact tips according to the invention, with that according to FIG. 2 being made chisel-shaped in the vicinity of the tip and used for treating hollow organs. The conically tapering contact tip according to FIG. 3 is used for pointwise vaporization; the one in FIG. 4 with for unilateral vaporization in hollow organs.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. Laser surgical apparatus for contact vaporization of tissue comprising:
   a light guide with a quartz glass core;
   a contact tip comprising a quartz glass sheath, said contact tip being arranged at a distal end of the light guide, with a distal end of the quartz glass core being fused with a distal end of the quartz glass sheath to form an optically transparent tip, wherein:
   the quartz glass core of the light guide runs coaxially with and is separated from an inside wall of the quartz glass sheath, by an axially extending gap; and
   a transition region of the quartz glass core at a distal end thereof has a diameter which increases, thereby decreasing a width of said gap, with increasing proximity to said optically transparent tip.

2. Apparatus according to claim 1 wherein the transition region has a jacket surface with curvature that increases steadily in the direction of a broader end thereof.

3. Apparatus according to claim 1 wherein the optically transparent tip has a shape which is selected from the group consisting of hemispherical, wedge-shaped and cone-shaped.

4. Apparatus according to claim 1 wherein a proximal end of the quartz glass sheath is glued to the light guide by means of an adhesive.

5. Applicator according to claim 4 wherein an index of refraction of the adhesive is lower than an index of refraction of the fiber core.

6. Apparatus according to claim 4 wherein a proximal end of the quartz glass sheath, at least in an area of the gluing to light guide, has a radiation-reflecting layer.

7. Apparatus according to claim 1 wherein laser light emerges from the entire surface of optically transparent tip.

8. Apparatus according to claim 1 wherein a length of a part of the quartz glass sheath that is not fused with quartz glass core of light guide is at least 10 mm.

* * * * *